(12) United States Patent
Peterson et al.

(10) Patent No.: US 6,620,169 B1
(45) Date of Patent: Sep. 16, 2003

(54) TOOLS AND METHOD FOR PROCESSING AND INJECTING BONE GRAFT

(75) Inventors: Francis C. Peterson, Prescott, WI (US); Stephen D. Kuslich, Stillwater, MN (US)

(73) Assignee: Spineology Group, LLC., Stillwater, MN (US)

( * ) Notice: Subject to any disclaimer, the term of this patent is extended or adjusted under 35 U.S.C. 154(b) by 221 days.

(21) Appl. No.: 09/645,422

(22) Filed: Aug. 24, 2000

Related U.S. Application Data

(60) Provisional application No. 60/150,835, filed on Aug. 26, 1999.

(51) Int. Cl.[7] ............................................. A61B 17/58
(52) U.S. Cl. ............................................. 606/93; 606/94
(58) Field of Search ........................... 606/93, 92, 94, 606/95, 99, 102, 86, 181; 623/23.48, 23.46, 23.21, 23.22, 23.62, 23.73, 22.12

(56) References Cited

U.S. PATENT DOCUMENTS

| | | | | |
|---|---|---|---|---|
| 4,277,184 A | | 7/1981 | Solomon | 366/150 |
| 4,576,152 A | | 3/1986 | Muller et al. | 128/92 |
| 4,655,749 A | * | 4/1987 | Fischione | |
| 4,671,263 A | * | 6/1987 | Draenert | |
| 4,815,454 A | | 3/1989 | Dozier, Jr. | 128/92 |
| 5,329,846 A | | 7/1994 | Bonutti | 100/50 |
| 5,431,654 A | * | 7/1995 | Nic | |
| 5,514,135 A | * | 5/1996 | Earle | |
| 5,545,222 A | | 8/1996 | Bonutti | 623/11 |
| 5,662,710 A | | 9/1997 | Bonutti | 623/11 |
| 5,697,932 A | * | 12/1997 | Smith et al. | 606/80 |
| 5,702,454 A | | 12/1997 | Baumgartner | 623/17 |
| 5,718,707 A | | 2/1998 | Mikhail | 606/94 |
| 5,741,265 A | | 4/1998 | Chan | 606/94 |
| 5,888,219 A | | 3/1999 | Bonutti | 623/11 |
| 6,395,007 B1 | * | 5/2002 | Bhatnagar et al. | 606/86 |
| 6,450,992 B1 | * | 9/2002 | Cassidy, Jr. | 604/164.01 |

OTHER PUBLICATIONS

Cheung et al., "*A bone graft condensing syringe system for maxillofacial reconstructive surgery*", vol. 35, pp. 267–270 (1997).
Robert E. Marx, and Marke E. Wong, "*A Technique for the Compression and Carriage of Autogenous Bone During Bone Grafting Procedures*", vol. 45, at p. 988–989 (1987).
Lambert et al., "*Modified Technique for Removal of a Compressed Particulate Bone Graft From a Syringe*", pp. 773–774 (1994).
R. Bilie and K. Korzinek, "*Results of Scaphoid Non–Union Treatment by the Matti–Russe Procedure Using Compressed Cancellous Bone*," pp. 134–138, (1987).

\* cited by examiner

*Primary Examiner*—Pedro Philogene
(74) *Attorney, Agent, or Firm*—Vidas, Arrett & Steinkraus PA

(57) ABSTRACT

A tool for processing an supplying bone graft material in individual tubes for later extrusion into the surgical site includes a pneumatic press and plunger to morselize and fill a plurality of fill tubes. The fill tubes are then used at the surgical site by pressing the bone material out with a push rod.

4 Claims, 3 Drawing Sheets

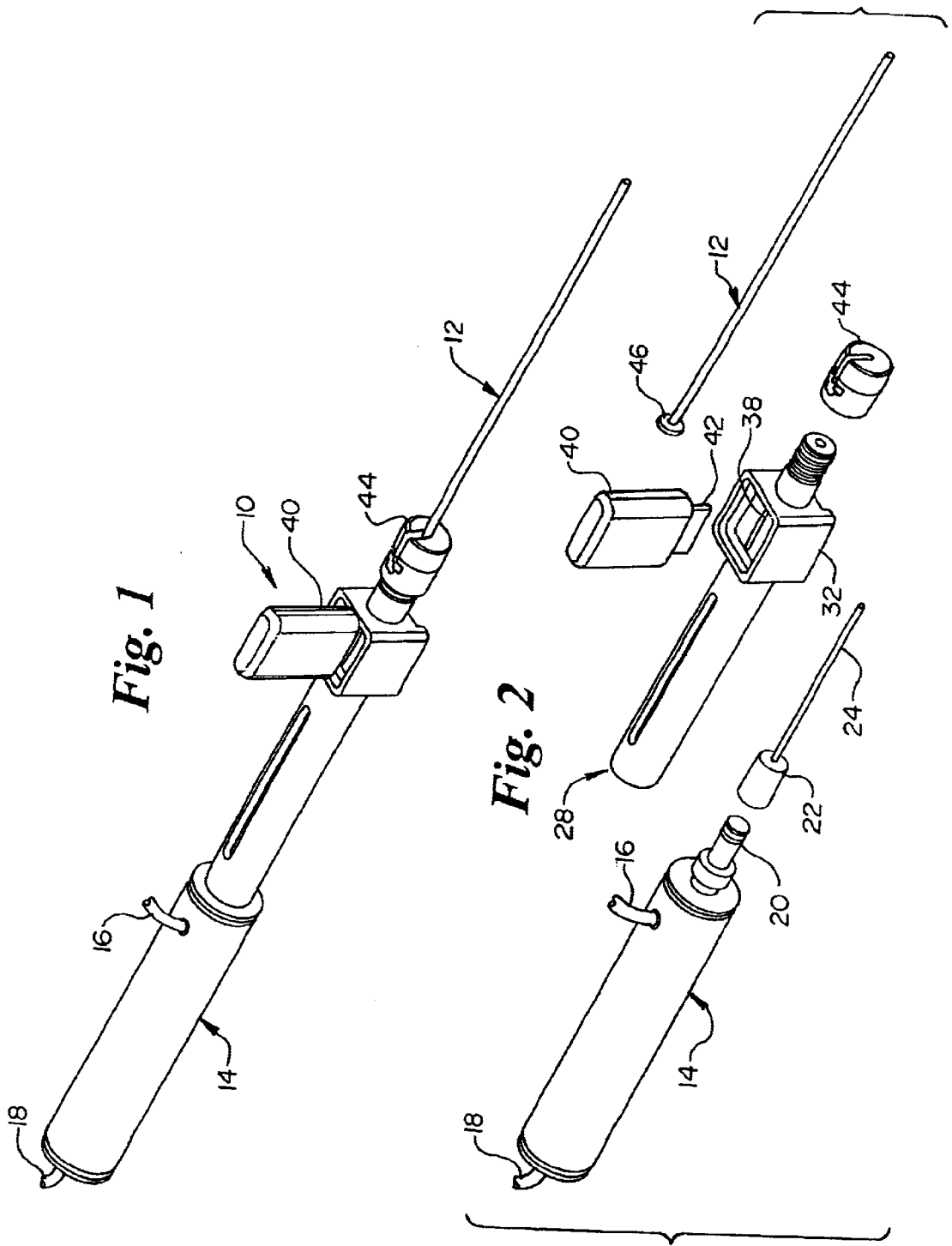

TOOLS AND METHOD FOR PROCESSING AND INJECTING BONE GRAFT

CROSS-REFERENCE TO RELATED APPLICATIONS

U.S. Provisional Patent Application No. 60/150,835 filed Aug. 26, 1999.

STATEMENT REGARDING FEDERALLY SPONSORED RESEARCH OR DEVELOPMENT

Not Applicable.

BACKGROUND OF THE INVENTION

This invention relates to a tool for preparing bone graft material by loading it into multiple tubes that may then be injected into a site needing bone graft material.

Bone graft material is typically harvested from a portion of a patient's body, such as a hip, and are used in repair procedures in another site, such as in fusing adjacent vertebra. Cheung et al, in the British Journal of Oral & Maxillofacial Surgery, Volume 35, pages 267–270 (1997) describe a bone graft condensing syringe system which uses a metal syringe, a plugger and a screw on cap along with a metal filling funnel to provide bone graft. Marx & Wong describe the use of a plastic syringe in J. Oral Maxillofacial Surgery, Volume 45, at pages 988–989 (1987) which compacts the bone graft material. A scalpel is required to cut off the needle end of the syringe to extrude out the graft material. Lambert et al., in Journal of Oral Maxillofacial Surg., pages 773–774 (1994) describe a syringe system employing a vented steel disc at the hub end of the syringe. The syringe is filled with bone, compressed with a plunger and extruded out with a steel rod through the hub which pushes out the disc and bone.

A series of Bonutti patents, U.S. Pat. Nos. 5,329,846; 5,545,222; 5,662,710 and 5,888,219 deal with a bone preparation system that uses a press to remove fluid from human tissue and insert the human tissue back into the person. The tissue may be bone.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

The invention provides a tool into which bone graft material is inserted. A ram in the tool fills tubes with the bone graft material. The filled tubes are then used to deploy bone graft material where needed with a second tool pressing the graft material out of the tubes. The tool and fill tubes provide the surgeon with prefilled tubes of known volume for surgical procedures which may be readily extruded into the surgical site.

BRIEF DESCRIPTION OF THE DRAWINGS

A detailed description of the invention is hereafter described with specific reference being made to the drawings in which:

FIG. 1 is a perspective view of the bone processing tool;

FIG. 2 is a perspective view of the bone processing tool of the invention exploded;

DETAILED DESCRIPTION OF THE INVENTION

Figure 3:
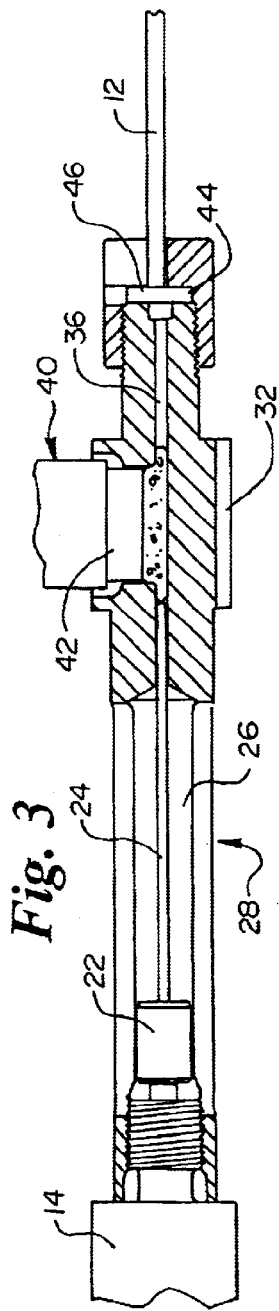
FIG. 3 is a side elevational view of the bone processing tool with parts cut away to show showing the tamper loading in bone.
Figure 4:
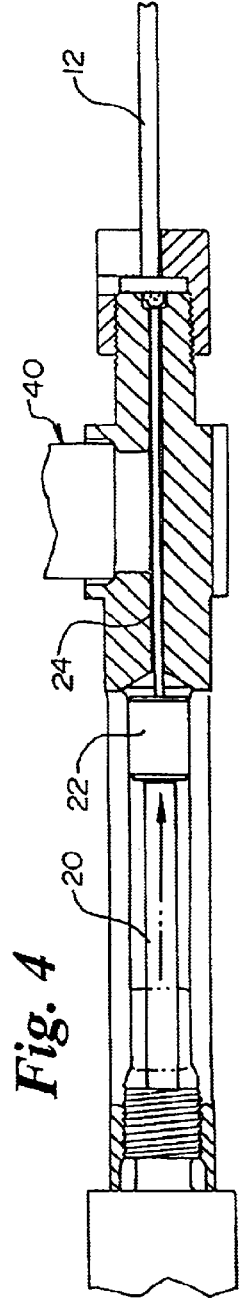
FIG. 4 is a side elevational view of the bone processing tool with parts cut away to show showing the plunger filling a fill tube with bone.
Figure 5A:
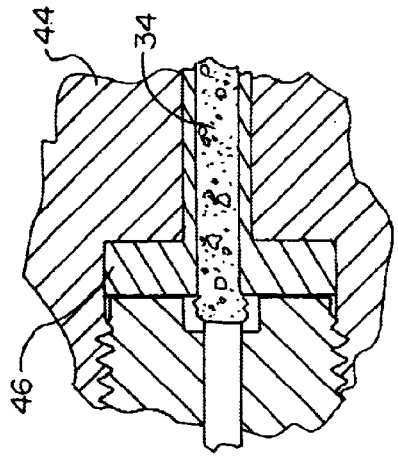
FIG. 5a is a partial enlarged view of the fill tube holder of FIG. 4 showing bone pushed into the fill tube by the plunger.
Figure 5:
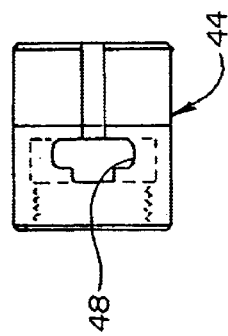
FIG. 5 is a side elevational view of the fill tube holder.
Figure 6:
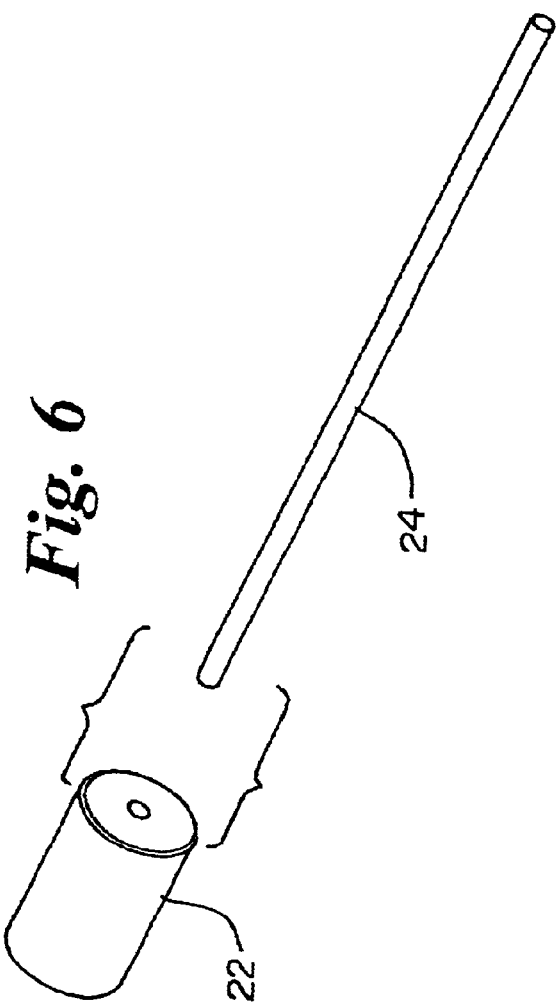
FIG. 6 is an exploded perspective view of the plunger and plunger rod.
Figure 7:
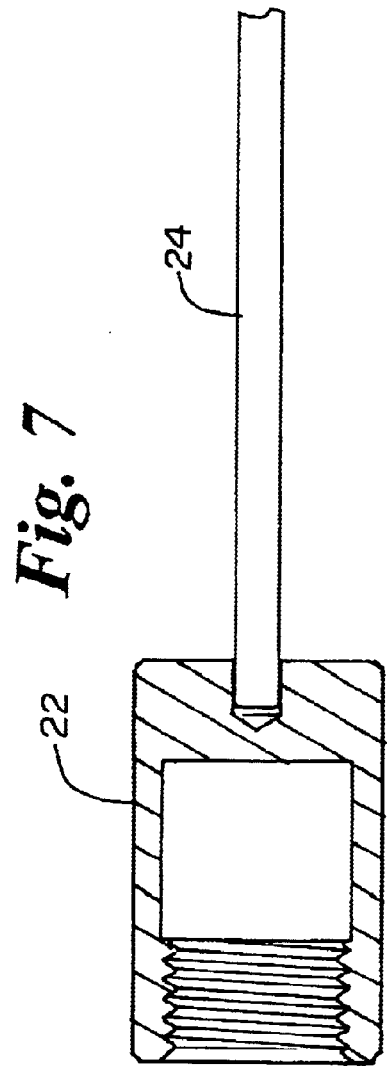
FIG. 7 is a cross-sectional view of the plunger.

Many surgical procedures involve the use of bone graft material. Depending on the surgery, the bone graft material may simply be harvested and placed into the situs with little difficulty. However, many procedures require relatively accurate placement of a known volume of morselized bone into the site, such as with in U.S. Pat. Nos. 5,571,189 and 5,549,679 to an expandable fabric bag for stabilizing the spinal motion segment and various cages such as shown in U.S. Pat. No. 5,489,308; 5,059,193 to Kuslich; U.S. Pat. No. 4,501,269 to Bagby and U.S. Pat. No. 4,743,256 to Brantigan.

It has been found that bone graft media tends to jam tubes when the tubes are larger in diameter. Thus, while it is possible to fill a syringe with bone material, the end must be cut off to access the bone material. This cutting step can cause an unwanted injury unless performed very carefully.

Any taper in a fill tube will tend to cause a channel blockage, even if very high hydraulic pressures are applied. Strangely, the inventors have discovered that too large a diameter allows plugs to form. Smaller tubes have less wall surface area and require less pressure to fill.

The fill tubes are preferably short enough to handle easily, the preferred length should be about 11" (27.94 cm) or less. A 0.014" (0.355 mm) diameter tube has an area of 0.010 sq. inches (6.4 mm$^2$), a circumference of about 0.76" (1.93 cm) and 50 pounds (22.7 kg) of hand pressure results in 5000 psi (34,473 kPa) within the tube. In contrast, a larger 0.025" (0.635 mm) diameter fill tube has a circumference of 1.57" (3.988 cm), and area of 0.049 sq. inches (31.6 mm$^2$) and 50 pounds (22.7 kg) of hand pressure results in 1020 psi (7,032 kPa). There is a relationship between force to diameter, diameter to friction, with length increasing friction.

The fill tubes distal ends are either entirely open or have a tool that mates with a specific cage to be filled. The proximal end of the fill tubes has a fixture for holding and securing to the filling tube device. The tubes inside diameter may be constant or slightly flared greater distally such that the diameter increases gradually from the proximal to the distal end. Otherwise, the bone material forms arches of particles, generating arch bridge-like strength causing the material to jam. Slots in the filling tool allows debris to fall back out from the filling process. Starting friction is overcome by pneumatic pressure, with air couplings to the piston providing the force to move the bone material into the fill tubes.

The ability to prepare a number of known volume tubes with bone material that will not jam provides a great advantage to the surgeon. They may be prepared ahead of time and may be used one after the other until the procedure is completed. The fill tubes provide a means for safely and quickly delivering a known quantity of bone material to a specific site. A push rod may be used to eject the bone material from the fill tubes into the surgical site by the surgeon.

With reference to the Figures, FIG. 1 shows the bone processing tool 10 with a fill tube 12 attached. The bone processing tool 10 includes a pneumatic cylinder 14 and piston 20 which is driven by an air supply and control through attachments 16, 18. The controls of the air supply are completely conventional and need not be illustrated herein. The cylinder 14 drives a piston 20 back and forth, which in turn moves plunger 22 and plunger rod 24 back and forth within chamber 26 of housing 30. Housing 30 includes a region 32 in which bone graft material 34 may be inserted into a narrow slot 38 that leads to a small channel 36 into which plunger rod 24 moves. A bone graft tamper 40 with a tab 42 sized to mate with slot 38 may be used to tamp the bone material into the channel 36. The fill tubes are attached to the proximal end of the tool via a fill tube holder 44. The fill tubes 12 have an elongated shaft and a flared distal end 46 which mates with a receptacle 48 in the fill tube holder 44.

In operation, a new fill tube 12 is attached to the tool 10, bone graft material 34 is tamped into slot 38 down into channel 36 by tamper 40 and the cylinder is cycled to cause the plunger to push the bone material into the fill tube. The process is repeated until the fill tube 12 is filled, which may be determined by observing bone graft exiting the proximal end of the fill tube 12.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A tool for filling tubes with bone graft material comprising:

(a) a pneumatic cylinder, piston, plunger, and plunger rod constructed and arranged such that an air supply in the cylinder causes the piston and the plunger to reciprocally travel within a housing that includes an access port into which bone graft material may be tamped into a channel in which the plunger reciprocates; and (b) a fill tube removably attached to said housing and in fluid communication with said channel such that movement of said plunger causes material within said channel to fill said fill tube.

2. The tool of claim 1 wherein the pneumatic cylinder is cycled to force the plunger forward and back in a reciprocating manner such that with each cycle the most recently tamped bone graft material is cleared from the channel and forced into the fill tube.

3. The tool of claim 1 further including a tamping block with a tab sized to mate with a slot in said housing through which the bone graft material enters said channel.

4. The tool of claim 1 further including said fill tube holder, said fill tube including a flared distal end, said fill tube holder being constructed and arranged to secure said fill tube flared distal end to said tool such that movement of said plunger causes material within said channel to fill said tube.

* * * * *